United States Patent
Decker

(10) Patent No.: US 10,814,123 B2
(45) Date of Patent: Oct. 27, 2020

(54) EMS STIMULATION CURRENT TRANSMISSION ELEMENT AND EMS GARMENT EQUIPPED WITH THE EMS STIMULATION CURRENT TRANSMISSION ELEMENT

(71) Applicant: Miha Bodytec GmbH, Gersthofen (DE)

(72) Inventor: Jürgen Decker, Emersacker (DE)

(73) Assignee: Miha Bodytec GmbH, Gersthofen (DE)

( * ) Notice: Subject to any disclaimer, the term of this patent is extended or adjusted under 35 U.S.C. 154(b) by 298 days.

(21) Appl. No.: 15/618,015

(22) Filed: Jun. 8, 2017

(65) Prior Publication Data

US 2017/0274199 A1    Sep. 28, 2017

Related U.S. Application Data

(63) Continuation of application No. PCT/EP2015/025074, filed on Oct. 27, 2015.

(30) Foreign Application Priority Data

Dec. 18, 2014  (DE) ................. 10 2014 018 683

(51) Int. Cl.
*A61N 1/04* (2006.01)
*A61N 1/36* (2006.01)

(52) U.S. Cl.
CPC ........... *A61N 1/0452* (2013.01); *A61N 1/048* (2013.01); *A61N 1/0484* (2013.01); *A61N 1/36003* (2013.01)

(58) Field of Classification Search
CPC .. A61N 1/0452; A61N 1/36003; A61N 1/048; A61N 1/0484
See application file for complete search history.

(56) References Cited

U.S. PATENT DOCUMENTS 3,610,250 A  10/1971 Sarbacher
3,662,757 A   5/1972 Blackett
(Continued)

FOREIGN PATENT DOCUMENTS

CN  200980675  11/2007
DE    2018239  11/1970
(Continued)

OTHER PUBLICATIONS

International Search Report dated Mar. 2, 2016 of international application PCT/EP2015/025074 on which this application is based.
(Continued)

*Primary Examiner* — Mark Bockelman
(74) *Attorney, Agent, or Firm* — Falk Ewers; Ewers IP Law PLLC

(57) ABSTRACT

An EMS stimulation current transmission element for an EMS garment includes a planar current transmission region of an EMS electrode for transmitting EMS stimuli to the living body, which contains a number of two-dimensionally arranged linear current conductor strand sections and is connected, via a further number of linear current conductor strand sections, to a connection point that is in particular spaced apart from the current transmission region, at which connection point the EMS stimulation current transmission element can be connected to an EMS stimulation current production unit, in order to load the current transmission region with an EMS stimulation current shaped by the EMS stimulus current production unit from a current drawn from a current source to form a pulse sequence and/or to form an alternating current. The current transmission region has a single linear current conductor strand section. An EMS garment has an EMS stimulation current transmission element.

11 Claims, 4 Drawing Sheets

(56) References Cited

U.S. PATENT DOCUMENTS

| | | | |
|---|---|---|---|
| 4,265,253 A * | 5/1981 | Abraham | A61N 1/0456 607/152 |
| 4,509,535 A * | 4/1985 | Bryan | A61N 1/0472 607/152 |
| 4,729,377 A | 3/1988 | Granek et al. | |
| 5,285,781 A | 2/1994 | Brodard | |
| 6,019,877 A | 2/2000 | Dupelle et al. | |
| 6,169,922 B1 * | 1/2001 | Alferness | A61F 2/2481 600/16 |
| 6,550,652 B2 * | 4/2003 | Whitaker | A01K 11/00 224/191 |
| 6,845,272 B1 | 1/2005 | Thomsen et al. | |
| 7,097,746 B1 | 8/2006 | Tziviskos et al. | |
| 7,499,747 B2 * | 3/2009 | Kieval | A61N 1/0556 607/1 |
| 9,067,199 B2 | 6/2015 | Nesterenko et al. | |
| 2002/0077688 A1 | 6/2002 | Kirkland | |
| 2002/0077689 A1 | 6/2002 | Kirkland | |
| 2002/0099320 A1 | 7/2002 | Beck | |
| 2004/0009731 A1 | 1/2004 | Rabinowicz | |
| 2005/0246002 A1 | 11/2005 | Martinez | |
| 2009/0105795 A1 | 4/2009 | Minogue et al. | |
| 2013/0085538 A1 * | 4/2013 | Volpe | A61N 1/3975 607/6 |
| 2015/0202429 A1 | 7/2015 | Fritzsche | |

FOREIGN PATENT DOCUMENTS

| | | |
|---|---|---|
| DE | 20209219 U1 | 10/2002 |
| DE | 10248235 A1 | 5/2004 |
| DE | 202004004582 U1 | 6/2004 |
| DE | 102005058850 A1 | 6/2007 |
| DE | 102007046886 A1 | 4/2009 |
| DE | 102009017179 A1 | 12/2010 |
| DE | 202011050682 U1 | 11/2011 |
| DE | 202011109226 U1 | 9/2012 |
| DE | 102012112153 A1 | 6/2014 |
| EP | 0128103 A1 | 12/1984 |
| EP | 0459945 B1 | 11/1997 |
| EP | 0965358 A2 | 12/1999 |
| EP | 2024020 A1 | 2/2009 |
| WO | 2004006700 A1 | 1/2004 |
| WO | 2005107849 A1 | 11/2005 |
| WO | 2007138071 A1 | 12/2007 |
| WO | 2011089263 A1 | 7/2011 |
| WO | 2011118918 A2 | 9/2011 |
| WO | 2014000736 A2 | 1/2014 |

OTHER PUBLICATIONS

U.S. Appl. No. 15/450,018, filed Mar. 5, 2017, Hansjürger Horter.
U.S. Appl. No. 15/604,532, filed May 24, 2017, Hansjürgen Horter.

* cited by examiner

EMS STIMULATION CURRENT TRANSMISSION ELEMENT AND EMS GARMENT EQUIPPED WITH THE EMS STIMULATION CURRENT TRANSMISSION ELEMENT

CROSS REFERENCE TO RELATED APPLICATIONS

This application is a continuation application of international patent application PCT/EP2015/025074, filed Oct. 27, 2015, designating the United States and claiming priority to German application 10 2014 018 683.0, filed Dec. 18, 2014, and the entire content of both applications is incorporated herein by reference.

TECHNICAL FIELD

The invention relates to an EMS stimulation current transmission element and an EMS garment equipped with the EMS stimulation current transmission element.

BACKGROUND

With Electrical Muscle Stimulation (EMS), partly also called electromyostimulation, muscles in the living body, generally for muscle buildup purposes, for example, in fitness centers or with personal trainers, are impinged with electric stimuli in order to strengthen the muscles. For generation of these EMS stimuli and/or the EMS stimulation current, EMS stimulation production devices are used which generally include an electrical pulse generator as well as an electronic control system.

The control system specifies a stimulation scheme according to which from a current drawn from a current source EMS stimuli are formed, being temporally distributed and distributed on a plurality of EMS electrodes of the EMS-training device. The EMS stimuli are comprised of the current pulses and/or alternating current with values such as amplitude and frequency predefined by the control system, and with which EMS electrodes attached to the body are impinged in order to lead current through the body with a predefined amplitude and frequency pattern. In this process, the EMS electrodes on the EMS garment are usually grouped in pairs so that two EMS electrodes grouped into such a pair are each connected to the EMS stimulation production unit via a line branch, wherein the two line branches during the EMS training through the body to which their EMS electrodes are attached, are completed into a closed circuit which passes through the body in a desired region, for example, through a thigh or an upper arm, and thus forces the muscles into contractions there, and thus strengthens them.

Thus, clocked pulse currents are produced in the EMS stimulation production unit and, via current lines, are passed to EMS electrodes and via the EMS electrodes passed through the body. In this process, generally the EMS electrodes are connected in pairs such that at one point in time a first EMS electrode is impinged with a current impulse, and a second EMS electrode is not impinged at that point in time, and allows the current passed through the body to flow off. In a pulse change, the second EMS electrode is impinged with a current impulse and the first EMS electrode is not impinged with current. The current flow path is still more complex in the case of a garment with several EMS electrode pairs, for example, breast, stomach, back, upper arms, thighs etc.

The EMS electrodes are interconnected with the EMS stimulation production unit, hence a control unit, which operates for example, in a frequency range of 2 to 150 Hz with a pulse width of 50 to 400 microseconds and a pulse break of 0 to 10 seconds. The maximum peak value of the electric output voltage is, for example, at 70 to 160 Volt at a current intensity of approximately 10 to 20 milliamperes.

Formerly, polymer pads filled with conductive particles (for example soot) were used as EMS electrodes to be attached to the body. Moreover, from diathermy, electrodes are known, which include a current transmission region and/or a conductive layer made of metal foil, which is backed with plastics. See U.S. Pat. No. 3,662,757.

But such EMS electrodes are not sufficiently flexible and elastic for today's EMS applications and it is difficult to integrate them into textile carriers. EMS electrodes are generally attached on an electrode carrier which can be placed on a body. While former electrode carriers often included belt and leather straps, see for example, DE 10 2005 058 850 A1, to which the electrodes were attached, and the requirements for electrodes with respect to flexibility, elasticity were low, the development is more and more towards textile EMS garments which carry the electrodes and/or into which the electrodes are integrated.

Such EMS garments can be worn by the exercising individual just like a garment, thus, for example, as a vest, trousers, stocking, arm band or the like and are often wetted prior to training or are worn over a wetted undergarment, for example, a T-shirt. Therein the EMS electrodes generally can include further structures above or behind the actual current transmission region and/or their conductive layer, which structures serve as a moisture storage. There are also textile EMS electrodes where the current transmission region with the moisture storage is combined in a common textile structure, such as can be taken, for example, from the German patent application DE 10 2007 046 886 A1. The EMS electrodes to be attached to the body, which are described there, have textile structures with integrated silver threads.

Apart from such external EMS electrodes and EMS electrodes to be attached to the EMS garment acting as a carrier, from the field of the thrombosis stockings and electromassage stockings and the like, electrodes integrated into textiles have already become known which are already woven or knitted or the like into the fabric of the EMS garment.

Thus, German utility model DE 202 09 219 U1 describes a knitting for a stocking with regions serving as electrodes into which conductive threads are knitted which include connection possibilities on defined endpoints for a measuring or supply voltage. Said conductive threads are silver-coated multifilament threads or stranded metal threads. Connection to the current supply occurs via conductive snap-fasteners, wherein the free ends of the conductive thread are bound by a fusion thread integrated into the knitting and subsequently molten.

Such electrodes are connected to the current supply by the snap-fasteners and/or in the case of EMS electrodes to the EMS stimulation production unit. Thus, EMS garments with several EMS electrodes get an unattractive appearance for the consumer because of the cable tangle. Moreover, the snap-fasteners tend inexplicably and randomly distributed in place and time to corrosion.

Concepts for electrodes known from the electromassage field, which are woven into the garment as conductive areas integrally with the supply lines and include a flexible, conductive fiber, see for example, the massage gloves and stockings shown in German utility model DE 20 2004 004 582 U1 and the international patent application WO 2011/118918 A2, have been adapted in order to eliminate the visible cables on EMS garments or at least to shorten the cables leading from the EMS garment to an external control unit.

Therefore, also EMS electrodes integrated into textiles exist today which are entirely integrated into the carrier textile or at least their current transmission region is integrated into the carrier textile, wherein apart from the electrodes also the track conductors connected to the electrodes are integrated into the EMS garment.

Hence the German printed utility model specification DE 20 2011 109 226 U1 describes an EMS garment with textile contact electrodes and/or EMS current transmission regions which are connected with an attributed connecting element in the form of a snap-fastener or the like via also textile-based supply lines integrated into the garment. The contact electrodes and/or the current supply regions can be made of a fabric out of silver threads and elastane or a silver fabric applied on a carrier material. Whereas fabric consists of a plurality of threads, namely warp threads and weft, knitted fabric is mesh material.

Moreover, German patent application DE 10 2012 112 153 A1 and the international patent application WO 2014/000736A2 show EMS electrodes integrated into textiles, the current transmission region of which is integrated into flat knitwear as an intarsia and connected with electricity by a connecting line likewise knitted in, which runs in a channel likewise knitted in. The intarsie have an implant towards the skin of the user which is preferably made of caoutchouc. It has to be noted here that an intarsia occurs by producing within a row of meshes individual sections of the row with different yarns (such as for example in the case of multicolored Norwegian sweaters). Thus, the intarsie are formed by meshes of the flat knitwear.

U.S. Patent Application Publication No. 2004/0009731 shows circular knitwear with knitted-in electrodes which can be knitted in together with the supply lines. Hence, the current transmission regions of the EMS electrodes but also the supply lines are each formed by a thread knitted into intertwined meshes, which forms linear current conductor strand sections from mesh row to mesh row along which current flow occurs. Thus, the current flow does not follow the pattern of the thread but jumps from mesh row to mesh row from one linear current conductor strand section of the thread to another linear current conductor strand section of the thread, which current conductor strand sections do not connect to each other in the strand formed by the thread.

Such EMS garments with EMS electrodes integrated into textiles may possibly be produced in one operation, which is not quite uncomplicated and presents challenges in the textile manufacturing process. Moreover, in the case of such EMS electrodes integrated into garment, a special focus is on the fact that they have high flexibility and possibly also elasticity since the EMS garments and together with them the EMS electrodes must lie close to the body. This flexibility and elasticity cannot be obtained with the conductive threads used for the fabrics and knitwear or can only be obtained in an expensive manner with expensive special threads which are conductive and elastic at the same time.

SUMMARY

It is an objective of the present invention to create an EMS stimulation current transmission element as well as an EMS garment equipped with the EMS stimulation current transmission element which are robust and remain operational over a long period of time, and which can be produced in a cost-effective manner with high flexibility and elasticity.

A generic EMS stimulation current transmission element for an EMS garment includes at least a planar current transmission region of an EMS electrode for transmitting EMS stimuli to the living body. The current transmission region contains a number of two-dimensionally arranged linear current conductor strand sections and is connected via a further number of linear current conductor strand sections to a connection point which is spaced apart from the current transmission region. The current conductor strand sections are linear contrary to a two-dimensional element such as, for example, a conductor foil but they need not necessarily be laid along straight lines. At the connection point, the EMS stimulation current transmission element can be connected to an EMS stimulation production unit in order to load the current transmission region with an EMS stimulation current shaped by the EMS stimulation current production unit from a current drawn from a current source to form a pulse sequence and/or to form an alternating current.

According to an aspect the invention, the current transmission region of the EMS stimulation current transmission element includes a single linear current conductor strand section which is laid in a two-dimensional or areal manner and without any meshes. Hence, on the surface of the current transmission region, a linear current conductor strand section is laid in such a way that it covers the surface. The linear current conductor strand section together with a linear current conductor strand section leading to the connection point is formed by single linear current conductor strand. Hence, the current flow follows the linear current conductor strand and does not jump from mesh to mesh and/or in the fabric. The EMS garment according to an aspect of the invention includes at least one such EMS stimulation current transmission element.

The invention is based upon the cognition that systemic faults on the connecting points of the current transmission regions with the supply lines can result in different resistances in the two-line branches allocated to each other because the connecting points are often formed as snap-fasteners or crimp connectors or knitwear not intermeshed or not entirely intermeshed. During production, it may occur that the mechanical connection is not correctly established which results in the fact that from an electrical viewpoint, an intermediate resistance occurs on the respective connecting point but possibly not in the opposite allocated line branch. But also a fabric and/or knitwear itself is susceptible to mesh faults or tear in the fabric and/or knitwear due to wear which can likewise result in an intermediate resistance and thus to different resistances in the two line branches allocated to each other.

Due to these differences in resistance, different flows in the current admission line branch opposite to the current discharge line branch occur which results in an electron release, for example, of the electrode material, of the electrode/current line contacting material or in the current line and thus finally leads to oxidation. This oxidation and thus corrosion occurring in different locations in the electric circuit where on the corrosion points the metallic material existing there oxidizes and thus corrodes under electron release acts itself now as if from an electrical viewpoint an intermediate resistance would be integrated on the corroding points. Over time, the oxidation and thus the increase of resistance can result in the fact that the EMS electrode arranged in the line branch concerned can no longer transmit any EMS stimulus required for the desired muscle contraction. Due to the sweat and/or the electrolytic effect of the sweat, this process is enhanced and accelerated.

According to an aspect of the invention, due to the configuration of the EMS electrode and/or its current transmission region together with the supply line by a single current conductor strand such an error-prone connecting point, be it realized as a snap-fastener/crimp connector or as a connection of two pieces of knitwear, is eliminated so that a large source of errors is avoided in the production process. Moreover, due to the unmeshed laying of the current conductor strand on a surface, a clearly higher elasticity of the total element can be achieved compared with mesh material or fabric. Furthermore, also the production of such an EMS stimulation current transmission element is quite simple and cost-effective, as will be explained still below.

According to another aspect of the invention, instead of a single current conductor strand also several current conductor strands to be supplied with current in parallel could be provided. Thus, the current transmission region includes a plurality of linear current conductor strand sections laid in parallel, which are each laid in a two-dimensional or areal manner without meshes, and which are formed each of a single linear current conductor strand with one of the current conductor strand sections leading to the connection point.

According to another aspect of the invention, the current transmission region could moreover include a plurality of linear current conductor strand sections laid in two-dimensional or areal manner and in parallel and without meshes, which are all spliced with the single linear current conductor strand section which leads to the connection point.

If, apart from the connection point for the current supply, a further ground connection point is necessary in order to divert a current transmitted to the current transmission region when impinging the EMS stimulation current onto the body or another connection point in order to supply current to the current transmission region in parallel from both ends of the current conductor strand, the current conductor strand section could be formed from the further connection point to the current transmission region analogously to the current conductor strand section from the connection point to the current transmission region integrally and in one piece on the single current conductor strand, which leads from the connection point to the current transmission region, through the current transmission region and then to the further connection point. Several parallel current conductor strands and a resplicing together of current conductor strand sections spliced open in the current transmission region would also be imaginable.

In order to lay, in a two-dimensional or areal manner, the current conductor strand sections, according to the first aspect of the invention, the single current conductor strand in the current transmission region, it is advantageous, if the EMS stimulation current transmission element includes a carrier element on which the current conductor strand sections, according to the first aspect of the invention the single current conductor strand are and/or is arranged. The carrier element is preferably formed as a flat fabric. According to the requested property of the EMS stimulation current transmission element, the carrier element can be elastic, non-elastic as well as insulating and/or provided with an insulating layer on one side or on both sides or it can be uninsulated. The carrier element can advantageously also be highly wash proof and flame retardant.

The current conductor strand sections and/or the single current conductor strand can then at least in the area of the current transmission region be sewn or embroidered onto the carrier element by another thread. The stitch length can vary here in order to achieve more or less flexibility on the current conductor strand and/or the track conductors. But it would also be imaginable to use the current conductor strand sections themselves and/or the single current conductor strand itself as sewing yarn for the seam and to sew or embroider it in this way into the textile carrier element.

The textile carrier element can be formed as an EMS garment, hence, for example, as a vest or trousers. But advantageously, the EMS stimulation current transmission element is provided with a carrier element on which it can be sewn into a garment. The carrier element can be cut out from a length of fabric or the like by laser cutting along the current conductor strand and/or strands laid on it, hence around the current transmission region and/or regions and the supply line.

The carrier element of the EMS stimulation current transmission element can advantageously be not electrically conductive or only poorly electrically conductive, in particular also in wetted condition so that in the condition of the EMS stimulation current transmission element sewn into or attached to the EMS garment, the carrier element can serve already as a rear insulation of the EMS electrode and/or its current transmission region. Alternatively, the EMS garment can include corresponding insulation structures which cover the EMS stimulation current transmission element in the current-carrying region.

In order to maintain the desired elasticity for the EMS stimulation current transmission element in total but in particular in the section covered by the current transmission regions and the supply lines, which can be achieved with a textile carrier material, for example, by the use of elastane, the current conductor strands forming the single current transmission regions plus supply line can be attached to the carrier element following a zigzag track or in a meandering manner, hence be advantageously sewn on or embroidered. If tensile stress is exercised on the corresponding current conductor strand section, it can yield like an accordion. It can be sufficient, if only the current conductor strand sections, which will probably be under tensile stress, are laid at least in sections following a zigzag track or in a meandering manner. Hence, the current conductor strand section and/or sections leading from the current transmission region to the spaced apart connection point and/or ground connection point could have the zigzag pattern.

In order to lay flat, the preferably only current conductor strand in the current transmission region, the current conductor strand will be laid in the current transmission region in total following a zigzag track with a plurality of subsequent parallel current conductor strand sections arranged next to each other and in an electrical serial connection. This does not only result in a good coverage of the surface of the current transmission region but at the same time an extensibility of the current conductor strand and the carrier textile in the current transmission region transverse to the direction into which the current conductor strand sections are laid there.

In order to maintain a corresponding elasticity and/or extensibility at the same time in the direction in which the current conductor strand sections extend in the current transmission region, the single current conductor strand sections in turn can each be laid following an own zigzag track and/or in a meandering manner extending with clearly smaller amplitudes compared with the total zigzag track in the current transmission region. For laying the current conductor strand sections in the current transmission region, these can be embroidered onto the textile carrier element and thus fixed in place.

Hence, by the embroidering forms (meandering track, straight line, extensive meandering track with straight or meandering track sections) different properties of the EMS stimulation current transmission element can be generated, wherein it is also always important here that the carrier material, which shall be used for the respective purpose, matches the purpose. Thus, by an extensive meandering track, a surface of a current transmission region of an EMS electrode can be generated and/or covered. By straight lines, for example, current track conductor sections can be realized, which shall not permit any elasticity (for example, at the supply line from the connection point to the current transmission region), and by current track conductor sections embroidered in a meandering manner, a certain degree of flexibility and elasticity can be permitted to these current track conductor sections. In addition, by the meandering and/or zigzag track, a maximum tensile stress limitation can be determined which occurs prior to achieving the maximum elastic limit of the carrier material. This means that the meandering current track conductor sections achieve their maximum yield point prior to the maximum elastic limit of the carrier material and, as the case may be, other integrated elastic materials so that a tearing of the carrier material and, as the case may be, other integrated elastic materials is prevented. This clearly increases the durability of the carrier material and, as the case may be, other integrated elastic materials.

The current conductor strand and/or strands can be executed as a single conductor, for example, consist of a single metal wire, or a metal-coated plastic fiber. But such single conductors are at a disadvantage compared with fiber composites with respect to pliability as well as flexibility and extensibility of the carrier textile connected with the single conductor. Therefore, advantageously each current conductor strand is formed by a composite of single fibers.

Generally, the use of a braid, preferably a braided mesh or a hose braiding as a current conductor strand would be imaginable, wherein the braid could include single conductors made out of metal or with metal coating or could consist of such single conductors. Generally, it would also be imaginable that the current conductor strand and/or strands or at least one of the current conductor strands includes a fabric tape or working band which includes single conductors made out of metal or with metal coating or consists of said single conductors.

But it has turned out to be advantageous, if the current conductor strand consists of a single yarn, doubled yarn, twist, cord or rope which includes single conductors made out of metal or with metal coating or consists of such single conductors or of a metal strand the single conductors of which are formed by twisted or plied metal wires or metal fibers or include such metal wires or metal fibers.

Some or all single conductors and/or single fibers within the compound of the current conductor strand could, for example, be formed as a tape yarn made of a metal-coated foil. But it has turned out that single conductors formed as a filament or staple fiber are more appropriate, in particular filaments, hence monofilaments or multifilaments made out of metal or out of metal-coated plastics.

In tests, it has turned out in particular that a multifilament yarn made out of special steel multifilaments is on the one hand cost-effective, on the other hand flexible, easy to be laid and sufficient with respect to the current conductor properties. But apart from special steel, generally also other materials such as silver, different Cu alloys and silver alloys are suitable for the single fibers. Also, mixtures of single fibers consisting of different materials in a fiber composite of the current conductor strand would be imaginable.

The individual monofilaments can have a diameter in the micrometer range, the multifilament yarn a diameter in the range of a tenth of a millimeter up to a single-digit millimeter range.

Because in view of an easy layability but also a low line resistance, the fiber composites used as a current conductor strand are not dimensioned too low in diameter, thus include a diameter by one order or several orders of magnitude larger compared with, for example, the threads used in the textile carrier element. Especially in the case of such relatively thick current conductor strands, the high bending capacity of the fiber bundles takes effect.

For example, a yarn has been proven as particularly suitable for the use according to an aspect of the invention in the EMS field, in particular a special steel yarn with a diameter in the range of 0.3 to 2 mm, for example, 0.75 to 1.05 mm, especially a special steel multifilament yarn twisted or plied out of several, preferably four individual yarns, where the individual yarns include 200 to 300, for example, 275 special steel filaments with a diameter of 10 to 15 µm, in particular 12 µm, wherein as a special steel a chromium, nickel, molybdenum alloy such as for example WNo. 1.4435 (X2CrNiMo18-14-3) can be used which has the additional advantage that it is not magnetizable.

The fiber composite used as a current conductor strand, in particular the yarn explained above, can moreover have a coating for corrosion protection. A perfluoroalkoxy (PFA) coating has been proven to be suitable for it. The corrosion protection coating contributes to suppress further the effect chain of differences in resistance caused by corrosion described above which in turn results in increased corrosion.

According to another aspect of the invention, the current conductor strand sections extending between the connection point and/or the ground connection point and the current transmission region are laid between the carrier element and a top layer. The top layer can be a textile flat fabric like the carrier element. If the top layer also in wetted condition is not or at least only poorly electrically conductive, it can serve as a cover of the current-carrying supply lines to the body. Moreover, the top layer permits a simple laying of the current conductor strand section by sewing it in between the top layer and the carrier element. In other words, the top layer and the carrier element are connected with each other by seams on both sides of the current conductor strand section so that the current conductor strand section in the "tube" thus created can be laid loosely or still be fixed further by embroidering.

According to yet another aspect of the invention, the top layer can cover the entire carrier element, except for the current transmission region. For this purpose, the top layer includes an opening exposing the current transmission region. The carrier element and the top layer can be sewed, glued and/or welded with each other along the edge of the opening. Advantageously, the current conductor strand sections, hence preferably the single current conductor strand in the current transmission region on the edge of the current transmission region is covered by the seam and/or gluing or welding point with which the carrier element and the top layer are sewed.

In a condition of the EMS stimulation current transmission element sewed, glued and/or welded into an EMS garment or on the EMS stimulation current transmission element itself, of course also a layer, for example, a textile layer, covering the current transmission region can be provided so that the current flow does not occur directly onto the human or animal body but through said top layer. In particular, for this purpose a water-retaining, non-insulating layer with good adaptation to the body shape would be imaginable (sponge, microfiber-fleece, deep pile etc.).

As has been mentioned at the beginning, today's EMS garments are often provided with a plurality of EMS electrode pairs in order to exercise a plurality of muscle groups wherein a pair of correlating EMS electrodes is allocated to each muscle section, which electrodes are located in a line branch extending from the EMS stimulation production unit to the body and in a line branch extending back from the body so that an electric circuit is formed by the respective muscle section. Therefore, the EMS stimulation current transmission element includes advantageously an even plurality of line branches of which each one includes a current transmission region and its connecting current conductor strand section(s) which is formed, as explained above, in each case by the current conductor strand sections of a current transmission region of a single current conductor strand, by current conductor strand sections laid next to each other of current conductor strands connected in parallel or by splicing a current conductor strand into single current conductor strand sections. In other words, each of the line branches is formed by a single current conductor strand laid flat in the current transmission region or by a current conductor strand spliced open, or by a plurality of current conductor strands connected in parallel and laid in parallel in the current transmission region. In that case, two of the line branches each are allocated to each other and equipped with current transmission regions corresponding to each other in order to form an electric circuit leading through a muscle section of the living body.

In order to be able to connect further external EMS electrodes to the EMS garment, for example, EMS electrodes placed on bracelets to an EMS vest, the EMS stimulation current transmission element moreover advantageously includes another even plurality of additional line branches which lead in each case from a connection point for connection to the EMS stimulation production unit to an electrode connection point spaced apart for connection to an external EMS electrode, and which do not contain an EMS electrode themselves.

The advantages of this further embodiment show themselves in particular when the line branches and the additional line branches end on a common connection point, preferably in a common connector. The cabling of all EMS electrodes with the EMS stimulation production unit can then be made with a common cable leading from the EMS stimulation production unit to the connection point on the EMS garment and/or the connector there.

For contacting on the connector, the braids and/or single fibers can be unraveled at the end of the line branches and soldered in the connector, connected or cast. There is also the possibility of crimping, soldering or screwing onto another conductor medium. The end of the braids or multifilaments could also be spliced into another conductor medium via a splicing procedure.

If the line branches and, if applicable, the additional line branches extend in a region located between the common connection point and the current transmission sections in parallel and adjacent to each other, and then fan out like a cable harness into the single current transmission sections, a compact and stable structure of the EMS stimulation current transmission element with short current conductor strands results.

BRIEF DESCRIPTION OF THE DRAWINGS

The invention will now be described with reference to the drawings wherein.

DESCRIPTION OF EXEMPLARY EMBODIMENTS

Figure 1:
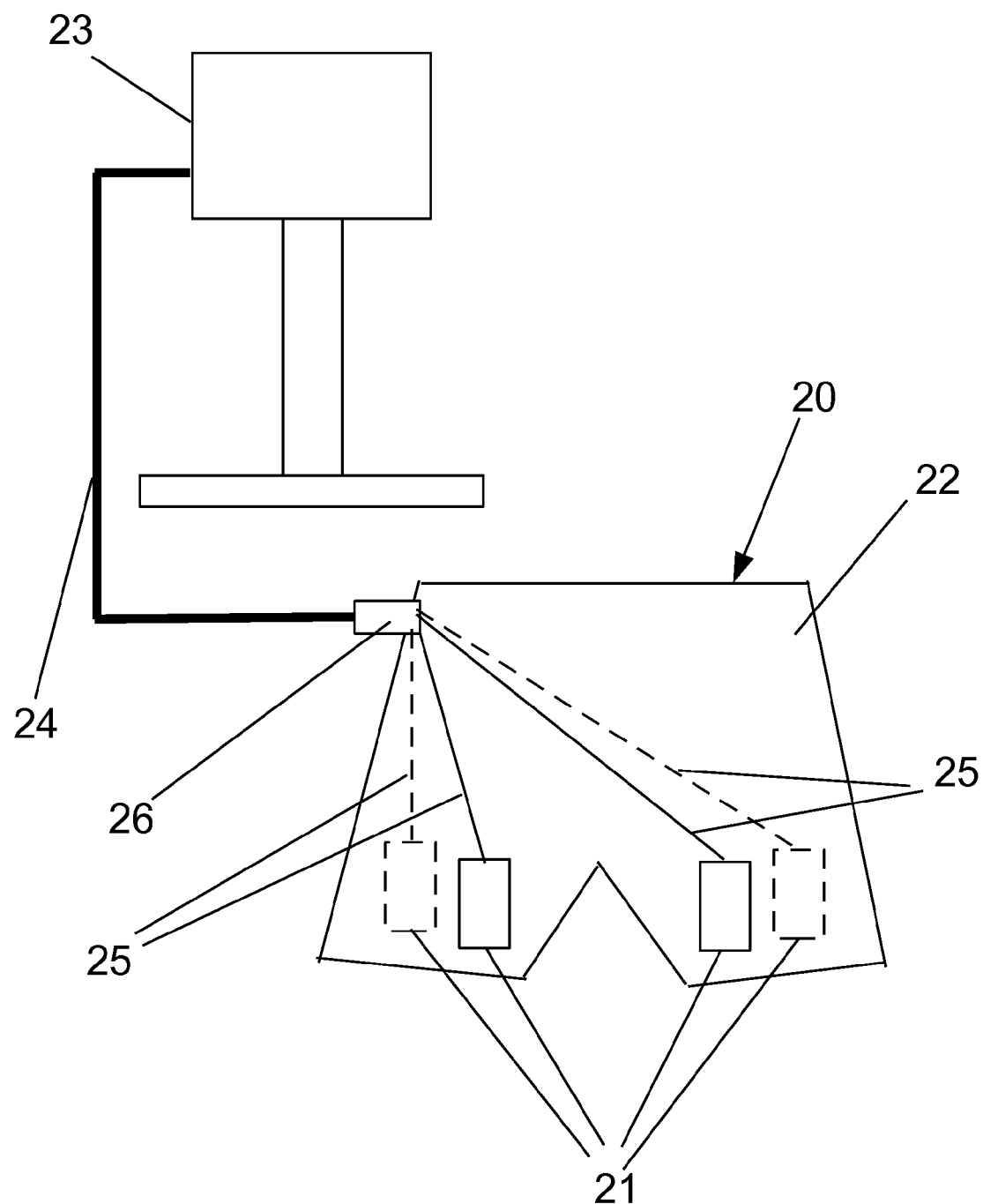
FIG. 1 shows a schematic view of an EMS training device with an EMS stimulation current transmission element configured as an EMS garment according to a first exemplary embodiment of the invention.

In FIG. 1, a stimulation current transmission element 20 configured as short trousers is shown which is equipped with four EMS electrodes 21 each grouped in two pairs, wherein each pair of electrodes is allocated to a thigh, and wherein each EMS electrode 21 via a current conductor strand section 25 is connected with a spaced apart connection point located in a connector 26. From the connector 26, a common signal cable 24 leads to an EMS stimulation production unit 23 built into a desk-shaped control unit. The EMS stimulation production unit 23 shapes EMS stimuli from a main current according to a desired excitation scheme and loads alternately the two EMS electrodes 25 of each pair of electrodes with it.

The EMS electrodes 21, the current conductor strand sections 25 and the connector 26 are placed on a textile carrier element 22. The current conductor strand sections 25 from the connector 26 to the EMS electrodes 21 and the EMS electrodes 21 themselves include a current conductor strand made from special steel yarn, which in turn includes some, for example, six, multifilament strands, and which in the region, covered by the allocated EMS electrodes 21, the current transmission region 21, is separated into its single multifilament strands, and laid flat there. The special steel yarn is embroidered onto the textile carrier element 22, and in the region of the current conductor strand sections 25 forming the connection lines 25 covered towards the inside, hence towards the body, with an electrically insulating top layer (not shown).

The carrier element 22, the EMS electrodes 21, the supply lines 25 and the connector 26 form an EMS stimulation current transmission element 20 which is already shaped as an EMS garment 20, namely short trousers.

The EMS stimulation current transmission element could of course also be shaped as an entirely different EMS garment, for example, as a vest or as a full body suit. A set of several EMS garments, for example, trousers, vests, bracelets, or lower leg bands could also be provided. The EMS stimulation current transmission element could of course also have an entirely different shape, for example, as an insert to be sewn into an EMS garment, as this is the case in the embodiment of the exemplary embodiment shown in FIG. 2.

Figure 2:
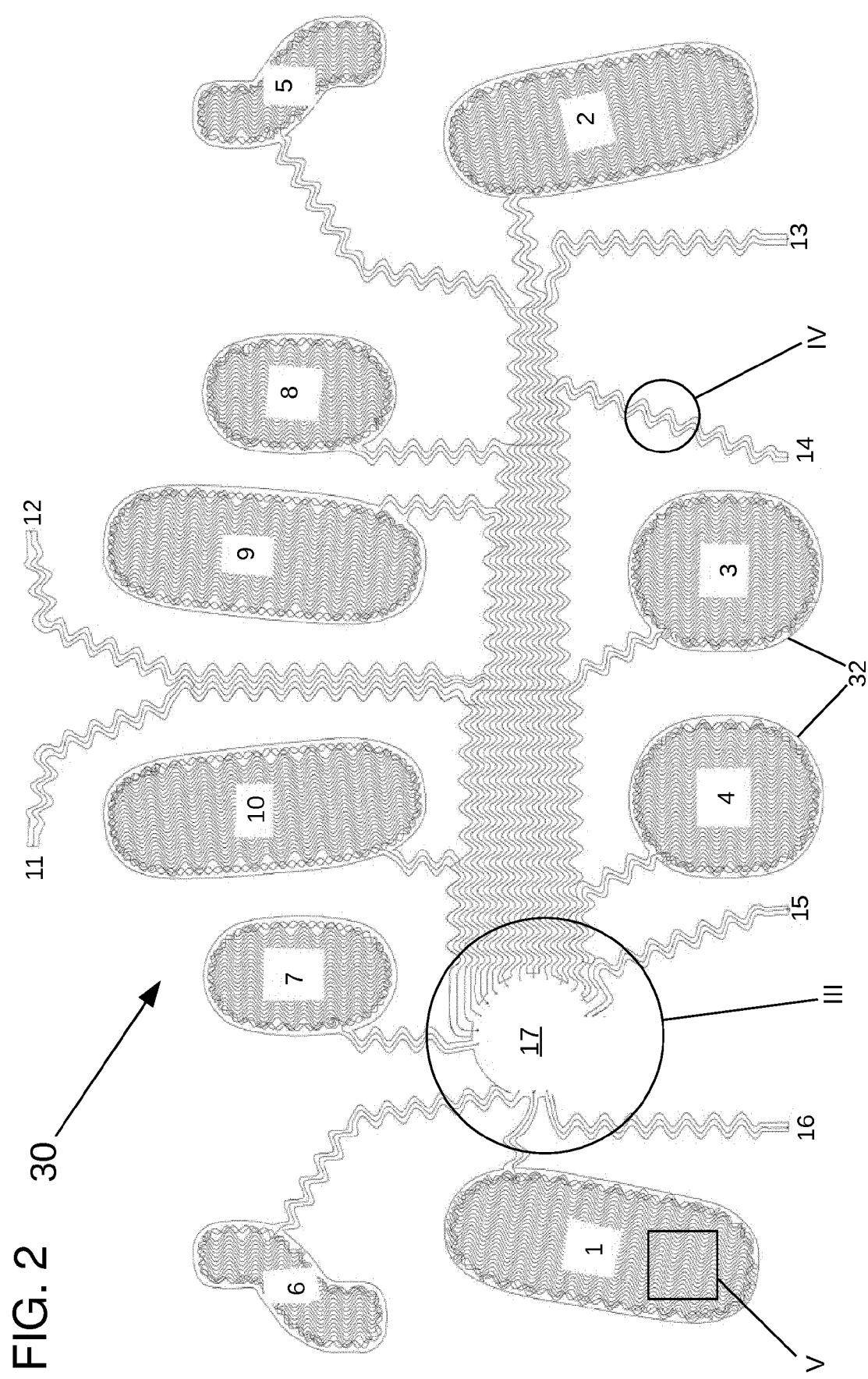
FIG. 2 shows a schematic view of an EMS stimulation current transmission element according to another exemplary embodiment of the invention configured for use as an EMS garment.

The EMS stimulation current transmission element 30 shown in FIG. 2 is designed as an insert to be sewn or glued into an EMS garment shaped as a vest, and for this purpose includes a carrier element 32 cut out from an unsewn circular knitted fabric along linear current conductor strands 1 to 16. The current conductor strands 1 to 16 have been embroidered onto the carrier element 32 in the shape shown prior to the cutting.

The current conductor strands 1 to 10 each lead from a common connection point 17 in a region in which they are each laid in a two-dimensional manner. These regions in which one of the current conductor strands 1 to 10 each is laid in a two-dimensional manner, in the state of the EMS stimulation current transmission element 30 sewn into the EMS garment, each serve as a current transmission region of an EMS electrode of the EMS garment. Thus, the line branches 1 to 10 which each contain an EMS electrode and the supply line from the connection point up to the EMS electrode are formed each by a single linear current conductor strand 1 to 10 preferably formed by a special steel multifilament yarn.

Two EMS electrodes each are allocated to each other wherein their current transmission regions correspond to each other in size, for example, the current transmission regions in the line branches 9 and 10. The two current transmission regions allocated to each other are located accordingly in two of the line branches 1 to 10, which are allocated to each other, for example, in the line branches 9 and 10, and form during the EMS training an electric circuit through the muscle section in the body to be trained, in the case of the line branches 9 and 10, for example, the rear trunk muscle sections.

Additional line branches 11 to 16, which are likewise formed by a single linear current conductor strand, namely from yarn, also start on the common connection point 17 and lead to free ends remote from it, where additional EMS electrodes for the extremities can be connected, for example, at 15 and 16 a pair of EMS electrodes for the one biceps, at 13 and 14 a pair of EMS electrodes for the other biceps. The cabling of the additional external EMS electrodes with the EMS stimulation production unit can then likewise occur via a connector to be attached on the common connection point 17.

Figure 3:
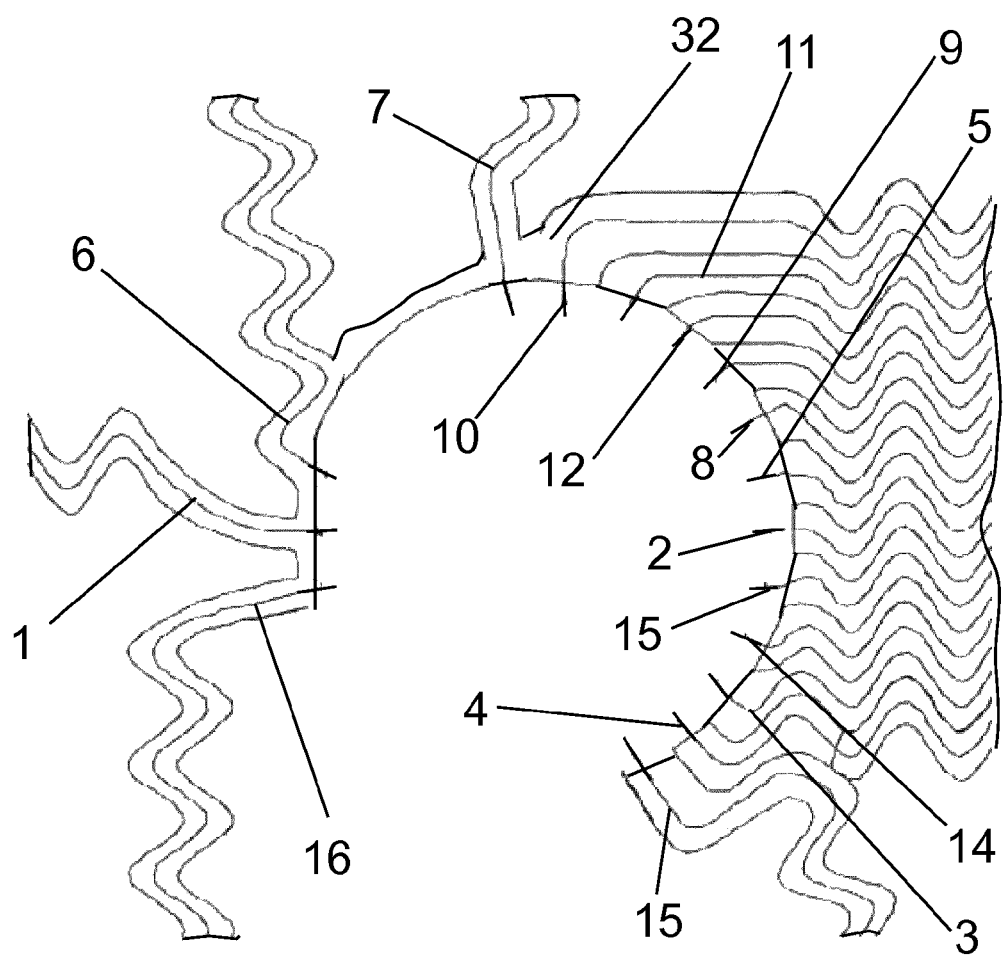
FIG. 3 shows detail III in FIG. 2.

The common connection point 17 is shown in FIG. 3 in detail. One recognizes the ends of the current conductor strands 1 to 16 which can, for example, be connected with a connector by a splicing procedure. Whereas the current conductor strands 1, 6, 7, 15 and 16 immediately extend on separate sections of the carrier element 32 there, which are only connected in the region of the common connection point 17 with the remainder of the carrier element 32, the other current conductor strands 2 to 5 and 8 to 14 extend at first in a common region and then fan out like a cable harness into single branches.

Figure 5:
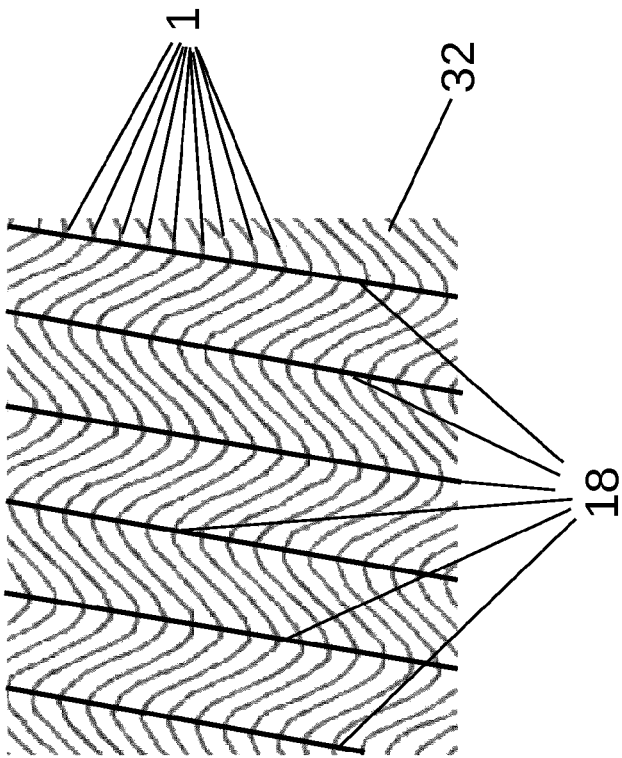
FIG. 5 shows detail V in FIG. 2.
Figure 4:
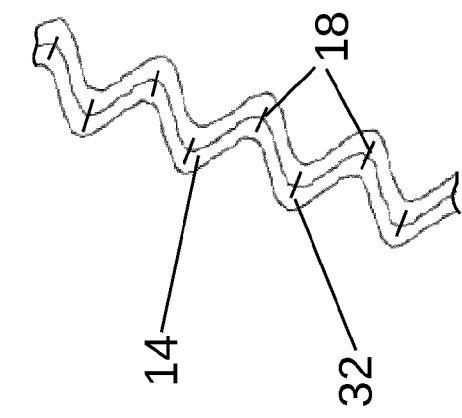
FIG. 4 shows detail IV in FIG. 2.

The current conductor strands 1 to 16 in their entire pattern (except for short supply lines on the common connection point 17) are embroidered onto the carrier element 32 in a meandering manner or in a zigzag track, as can particularly be seen in FIGS. 4 and 5 where the embroidering seams are each designated with reference numeral 18.

It is understood that the foregoing description is that of the exemplary embodiments of the invention and that various changes and modifications may be made thereto without departing from the spirit and scope of the invention as defined in the appended claims.

What is claimed is:

1. An EMS garment comprising:
    an EMS stimulation current transmission element with at least one EMS electrode to be attached to a living body for transmitting EMS stimuli to the living body and having a planar current transmission region, which contains a number of two-dimensionally arranged linear current conductor strand sections and is connected, via a further number of linear current conductor strand sections, to a connection point that is spaced apart from the current transmission region, at which connection point the EMS stimulation current transmission element can be connected to an EMS stimulation production unit in order to load the current transmission region with an EMS stimulation current shaped by the EMS stimulation current production unit from a current drawn from a current source to form a pulse sequence and/or to form an alternating current, wherein:
    the EMS electrode is formed by a single linear current conductor strand section, which is laid in the current transmission region in a two-dimensional manner without meshes, and together with the current conductor strand section leading to the connection point is formed by a single linear current conductor strand such that a connection of the current transmission region and the current conductor strand section leading to the connection point is avoided, or the EMS electrode is formed, instead of being formed by the single linear current conductor strand section, by a plurality of linear current conductor strand sections laid in the current transmission region in a two-dimensional manner and in parallel and without meshes and which are each formed by a single linear current conductor strand with one of the current conductor strand sections leading to the connection point such that the connection of the current transmission region and the current conductor strand section leading to the connection point is avoided, or
    the EMS electrode is formed, instead of being formed by the single linear current conductor strand section, by a plurality of linear current conductor strand sections laid in the current transmission region in a two-dimensional manner and in parallel and without meshes which are all spliced with the single linear current conductor strand section which leads to the connection point such that the connection of the current transmission region and the current conductor strand section leading to the connection point is avoided, and
    wherein the current conductor strand sections, or the single current conductor strand, is or are arranged on a carrier element formed as a textile flat fabric, and wherein the current conductor strand sections, or the single current conductor strand, at least in the region of the current transmission section, is sewn or embroidered onto the carrier element,
    wherein the carrier element is not electrically conductive and wherein the current conductor strand section(s) extending between the connection point and the current transmission region are laid between the carrier element and a top layer, and wherein the top layer is not electrically conductive.

2. The EMS garment according to claim 1, wherein the top layer comprises an opening exposing the current transmission region, wherein the carrier element and the top layer are sewn with each other along the edge of the opening, and wherein the current conductor strand sections, or the single current conductor strand, extend(s) on the edge of the current transmission region between the carrier element and the top layer.

3. The EMS garment according to claim 1, wherein the current transmission region comprises a plurality of current conductor strand sections laid in parallel next to each other, attached to the carrier element and each following a zigzag track or in a meandering manner.

4. An EMS garment comprising:
    an EMS stimulation current transmission element with at least one EMS electrode to be attached to a living body for transmitting EMS stimuli to the living body and having a planar current transmission region, which contains a number of two-dimensionally arranged linear current conductor strand sections and is connected, via a further number of linear current conductor strand sections, to a connection point that is spaced apart from the current transmission region, at which connection point the EMS stimulation current transmission element can be connected to an EMS stimulation production unit in order to load the current transmission region with an EMS stimulation current shaped by the EMS stimulation current production unit from a current drawn from a current source to form a pulse sequence and/or to form an alternating current, wherein:

the EMS electrode is formed by a single linear current conductor strand section, which is laid in the current transmission region in a two-dimensional manner without meshes, and together with the current conductor strand section leading to the connection point is formed by a single linear current conductor strand such that a connection of the current transmission region and the current conductor strand section leading to the connection point is avoided, or the EMS electrode is formed, instead of being formed by the single linear current conductor strand section, by a plurality of linear current conductor strand sections laid in the current transmission region in a two-dimensional manner and in parallel and without meshes and which are each formed by a single linear current conductor strand with one of the current conductor strand sections leading to the connection point such that the connection of the current transmission region and the current conductor strand section leading to the connection point is avoided, or the EMS electrode is formed, instead of being formed by the single linear current conductor strand section, by a plurality of linear current conductor strand sections laid in the current transmission region in a two-dimensional manner and in parallel and without meshes which are all spliced with the single linear current conductor strand section which leads to the connection point such that the connection of the current transmission region and the current conductor strand section leading to the connection point is avoided, and wherein the current conductor strand sections, or the single current conductor strand, is or are arranged on a carrier element formed as a textile flat fabric, wherein the current conductor strand sections, or the single current conductor strand, at least in the region of the current transmission section, is sewn or embroidered onto the carrier element, and wherein each current conductor strand is formed by a composite of single fibers, wherein each current conductor strand consists of a single yarn, doubled yarn, twist, cord or rope which comprises single conductors made out of metal or with metal coating or consists of such single conductors or of a metal strand the single conductors of which are formed by twisted or plied metal wires or metal fibers or comprises such metal wires or metal fibers.

5. The EMS garment according to claim 4, wherein each current conductor strand comprises single conductors formed as a filament or as a staple fiber, or consists of such single conductors, in particular comprises single fibers formed as monofilaments or preferably multifilaments made out of metal or out of metal-coated plastics, or consists of such single fibers.

6. The EMS garment according to claim 5, wherein the current transmission region comprises a plurality of current conductor strand sections laid in parallel next to each other, attached to the carrier element and each following a zigzag track or in a meandering manner.

7. The EMS garment according to claim 6, wherein the current conductor strand sections laid in parallel next to each in the current transmission region in an electrical serial connection successively form in total a zigzag track section of the single current conductor strand.

8. An EMS garment comprising:
an EMS stimulation current transmission element with at least one EMS electrode to be attached to a living body for transmitting EMS stimuli to the living body and having a planar current transmission region, which contains a number of two-dimensionally arranged linear current conductor strand sections and is connected, via a further number of linear current conductor strand sections, to a connection point that is spaced apart from the current transmission region, at which connection point the EMS stimulation current transmission element can be connected to an EMS stimulation production unit in order to load the current transmission region with an EMS stimulation current shaped by the EMS stimulation current production unit from a current drawn from a current source to form a pulse sequence and/or to form an alternating current, wherein:

the EMS electrode is formed by a single linear current conductor strand section, which is laid in the current transmission region in a two-dimensional manner without meshes, and together with the current conductor strand section leading to the connection point is formed by a single linear current conductor strand such that a connection of the current transmission region and the current conductor strand section leading to the connection point is avoided, or the EMS electrode is formed, instead of being formed by the single linear current conductor strand section, by a plurality of linear current conductor strand sections laid in the current transmission region in a two-dimensional manner and in parallel and without meshes and which are each formed by a single linear current conductor strand with one of the current conductor strand sections leading to the connection point such that the connection of the current transmission region and the current conductor strand section leading to the connection point is avoided, or the EMS electrode is formed, instead of being formed by the single linear current conductor strand section, by a plurality of linear current conductor strand sections laid in the current transmission region in a two-dimensional manner and in parallel and without meshes which are all spliced with the single linear current conductor strand section which leads to the connection point such that the connection of the current transmission region and the current conductor strand section leading to the connection point is avoided, and wherein the current conductor strand sections, or the single current conductor strand, is or are arranged on a carrier element formed as a textile flat fabric, wherein the current conductor strand sections, or the single current conductor strand, at least in the region of the current transmission section, is sewn or embroidered onto the carrier element, wherein the EMS stimulation current transmission element comprises an even plurality of line branches of which each one comprises a current transmission region and its connecting current conductor strand section(s), wherein each of the line branches is formed by a single current conductor strand laid in a two-dimensional manner in the current transmission region or by a current conductor strand spliced open, or by a plurality of current conductor strands laid in parallel in the current transmission region, and wherein two of the line branches each are allocated to each other and equipped with current transmission regions corresponding to each other in order to form an electric circuit leading through a muscle section of the living body.

9. The EMS garment according to claim 8, wherein the EMS stimulation current transmission element comprises another even plurality of additional line branches which lead in each case from a connection point for connection to the EMS stimulation production unit to an electrode connection point spaced apart for connection to an external EMS electrode, and which do not contain an EMS electrode themselves.

10. The EMS garment according to claim 9, wherein the line branches, and if applicable, the additional line branches end on a common connection point.

11. The EMS garment according to claim 10, wherein the line branches and, if applicable, the additional line branches extend in a region located between the common connection point and the current transmission regions in parallel and adjacent to each other, and then fan out like a cable harness into the single current transmission sections.

* * * * *